(12) United States Patent
Krzyzanowski (10) Patent No.: US 7,171,839 B2
(45) Date of Patent: Feb. 6, 2007

(54) METHOD OF MANUFACTURING A STAMPED BIOPSY FORCEPS JAW

(76) Inventor: Jacek Krzyzanowski, 17 Oxenden Crescent, Etobicoke, Ontario (CA) M9C 4H3

( * ) Notice: Subject to any disclaimer, the term of this patent is extended or adjusted under 35 U.S.C. 154(b) by 333 days.

(21) Appl. No.: 10/832,318

(22) Filed: Apr. 27, 2004

(65) Prior Publication Data
US 2005/0235725 A1    Oct. 27, 2005

(51) Int. Cl.
*B21D 31/00*    (2006.01)
*B21D 28/00*    (2006.01)

(52) U.S. Cl. ........................................ 72/379.2; 72/336

(58) Field of Classification Search ............. 72/379.2, 72/340, 341, 335, 336
See application file for complete search history.

(56) References Cited

U.S. PATENT DOCUMENTS

| | | | | |
|---|---|---|---|---|
| 5,133,727 A | * | 7/1992 | Bales et al. ............ | 606/170 |
| 5,647,115 A | * | 7/1997 | Slater et al. ............ | 29/557 |
| 5,707,392 A | * | 1/1998 | Kortenbach ............. | 606/207 |
| 6,378,351 B1 | * | 4/2002 | Ouchi et al. ............ | 72/336 |
| 6,440,085 B1 | * | 8/2002 | Krzyzanowski ......... | 600/564 |
| 2005/0054946 A1 | * | 3/2005 | Krzyzanowski ......... | 600/564 |

* cited by examiner

*Primary Examiner*—Lowell A. Larson
*Assistant Examiner*—Teresa M. Bonk
(74) *Attorney, Agent, or Firm*—Miller Thomson LLP (57) ABSTRACT

A method of progressive die stamping manufacturing a biopsy forceps jaw comprising the steps of cutting a sheet of metal into a strip. The strip of metal may then be punched with a series of guide holes. A shape larger than a pattern of the biopsy forceps jaw may then be defined in the strip of metal. An actuating hole may be punched into the shape. A concave shaped cup portion of the biopsy forceps jaw may be drawn. The pattern of the biopsy forceps jaw may then be cut to expose a cutting edge and exposed edges of the pattern. The cutting edge can be coined to provide a hardened, sharp, cutting edge. The exposed edges may be chamfered and then the pattern may be folded and shaped to form a biopsy forceps jaw cup and an arm positioned relative to the biopsy forceps jaw cup. A pivot hole may then be punched into the arm. The biopsy forceps jaw may then go through a calibration so that the cutting edge is in a plane perpendicular to a plane of the arm. The jaw cup may then be cut off of the strip of metal.

64 Claims, 6 Drawing Sheets

METHOD OF MANUFACTURING A STAMPED BIOPSY FORCEPS JAW

FIELD OF THE INVENTION

This invention relates in general to endoscopic instruments and more particularly to a method of manufacturing a stamped biopsy forceps jaw in a more cost efficient manner, thereby producing a superior product that allows for obtaining high quality tissue specimens.

BACKGROUND OF THE INVENTION

With the increased vigilance in infection control and the detection of new transmittable diseases, there is a need for disposable or single use biopsy forceps devices. Presently, the disposable and inexpensive biopsy forceps have jaws that may be made by either a casting method or through powder metal injection molding (MIM). Both methods can produce fairly inexpensive components, however due to the nature of the processes the biopsy jaws produced are of low quality. For instance the casting process does not produce jaws that have thin or very thin sections. This limitation reduces the capacity of the jaws and limits the size of the specimen that can be obtained. Furthermore, this method does not produce jaws that have sharp cutting edges and therefore does not have efficient biting capability. In U.S. Pat. No. 5,133,727 and related patents issued to Bales, Bales tried to overcome some of these problems by incorporating teeth at the cutting edge of the jaws. However, it is accepted in the industry that non-serrated, sharp jaws obtain better quality tissue specimen and provide for a better cut of the tissue, than jaws with the inclusion of teeth.

Jaws produced by MIM have thinner sections and sharper cutting edges, however the dimensional and geometrical repeatability of the parts is poor due to the extreme shrinkage of the parts during sintering process. Generally speaking, in order to produce precise jaws, one has to employ sophisticated CNC machining processes. However, these processes are prohibitively expensive for manufacturing single use instruments.

Prior art methods for manufacturing biopsy jaws have been developed to address some of the aforenoted problems, however these methods to do not disclose a method that produces biopsy forceps jaw with an improved cutting edge, is inexpensive to manufacture and is efficient to assemble. For example, U.S. Pat. No. 6,378,351 issued Apr. 30, 2002 to Ouchi, discloses a method for manufacturing a biopsy forceps cup for an endoscope in which a spoon-shaped forceps cup is formed by drawing a metal plate blank by a press. The method includes forming a first cut on the metal plate blank, wherein the first cut surrounds a contour of a portion of the metal plate blank defining a forceps cup blank corresponding to the forceps cup, the first cut being discontinued by a plurality of first connection portions. The method further includes forming a second cut on the metal plate blank, wherein the second cut surrounds the first cut, the second cut being discontinued by a plurality of second connection portions. The drawing operation on the metal plate blank is carried out while each of the first and second connection portions remain connected with respective neighbouring portions defined by each respective the first and second cuts. Ouchi clearly discloses the challenges and complexities of drawing a biopsy cup from a flat metal blank in a precise manner.

U.S. Pat. No. 5,707,392 issued Jan. 13, 1998 to Kornten-bach discloses a hermaphroditic biopsy forceps jaws for use in an endoscopic biopsy forceps instrument made from a flat sheet of stainless steel or other suitable material which is stamped and then progressively formed into a jaw cup having a tang. According to the preferred embodiment of the invention, the jaw is provided with two substantially parallel tangs, one being shorter than the other. Both tangs are provided with central mounting holes for mounting the jaw on an axle pin between the arms of a clevis. The longer of the tangs is provided with a hole for coupling it to the distal end of a control wire. The tangs are located such that when the jaws are mounted in the clevis, the short tang of each jaw resides between the two tangs of the other jaw. The stamped jaw of the invention may be provided with or without teeth. The location of the tangs permits the mounting of a knife between the jaws, if desired. Other end effectors of similar construction are also disclosed. The method disclosed in Kortenbach however has limited precision as the profile of the cup of the jaw is first cut and then drawn/formed to a spoon like shape.

Furthermore, the prior art has not been able to overcome the following challenges and problems illustrated in FIGS. 1–6, so as to produce or manufacture precise biopsy forceps jaws that have edges that closely match edge to edge when the jaws are in the closed position: overbite where one jaw is longer than the other; lateral shift caused by poor repeatability of the thickness of the arm of the jaw and/or its location; incorrect positioning of the pivot hole in relation to the plane of the cutting edge resulting in a large gap on both sides of the jaws when the tips of the cups meet, but the backs do not; or when the backs of the jaws meet, but the tips do not; a gap created when the cutting edge of the jaws meet on one side but not on the opposite side resulting from poor control of the perpendicularity of the cutting plane of the jaws to the arm, or a twist of the cup versus the arm; gaps between the jaws as a result of irregular cutting planes and or cutting edges; and/or a combination of any or all of the above mentioned problems.

Thus a method of manufacturing a stamped biopsy forceps jaw that produces inexpensive yet high quality biopsy jaw forceps that have precise matching of the jaw during closing and obtains excellent quality tissue samples and overcomes the problems outlined above is desirable.

SUMMARY OF THE INVENTION

An object of one aspect of the present invention is to provide an improved method of manufacturing a stamped biopsy forceps jaw.

In accordance with one aspect of the present invention there is provided a method of progressive die stamping for manufacturing a biopsy forceps jaw comprising the steps of cutting a sheet of metal into a strip. The strip of metal may then be punched with a series of guide holes. A shape larger than a pattern of the biopsy forceps jaw may then be defined in the strip of metal. A concave shaped cup portion of the biopsy forceps jaw may be drawn in the shape. The pattern of the biopsy forceps jaw may then be cut to expose a cutting edge and exposed edges of the pattern.

In accordance with another aspect of the present invention there is provided a method of progressive die stamping as described above further comprising coining the cutting edge to provide a hardened, sharp, cutting edge. The exposed edges may be chamfered and then the pattern may be folded and shaped to form a biopsy forceps jaw cup and at least one arm positioned relative to the biopsy forceps jaw cup. The arm may comprise of one or more lobes. At least one pivot hole (or pivot holes if the arm is comprised of more than one lobe) may then be punched into the arm. At least one actuating hole may be punched into the shape prior to drawing the concave shaped cup portion. The biopsy forceps jaw may then go through a calibration so that the cutting edge is in a plane perpendicular to a plane of the arm. The biopsy forceps jaw may then be cut off of the strip of metal in such a manner, that any consequent burr will protrude inwards.

Preferably the cutting edges may be coined to provide a hardened surface, however the cutting edges may also be serrated or thinned to improve biting action. A variety of different biting profiles exist depending on the requirement of the device. Conveniently the step of folding the pattern to form the biopsy jaw cup may be done simultaneously with the step of positioning the arm or this folding may be done separately.

Advantages of the present invention are: elimination of an overbite where one jaw is longer than the other; elimination of lateral shift caused by poor repeatability of the thickness of the arm of the jaw and/or its location; correct positioning of the pivot hole in relation to the plane of the cutting edge thereby eliminating a large gap on both sides of the jaws when the tips of the cups meet, but the backs do not; or the backs of the jaws meet, but the tips do not; elimination of a gap created when the cutting edge of the jaws meet on one side but not on the opposite side resulting from poor control of the perpendicularity of the cutting plane of the jaws to the arm, or a twist of the cup versus the arm; elimination of the gaps between the jaws as a result of irregular cutting planes and or cutting edges; and producing inexpensive yet high quality biopsy jaw forceps that have precise matching of the jaw during closing and obtains excellent quality tissue samples.

BRIEF DESCRIPTION OF THE DRAWINGS

A detailed description of the preferred embodiments are provided herein below by way of example only and with reference to the following drawings, in which:

FIG. 2b illustrates in a front plan the problem outlined in FIG. 2a.

FIG. 5b illustrates in a front plan the problem outlined in FIG. 5a.

FIGS. 18a–i are perspective views of the method in accordance with a preferred embodiment of the present invention.

In the drawings, preferred embodiments of the invention are illustrated by way of example. It is to be expressly understood that the description and drawings are only for the purpose of illustration and as an aid to understanding, and are not intended as a definition of the limits of the invention.

DETAILED DESCRIPTION OF THE PREFERRED EMBODIMENT

Figure 1:
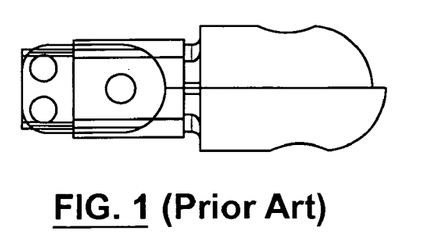
FIG. 1 illustrates in a side elevation view the problem of overbite, when one jaw is longer than the other.
Figure 2A:
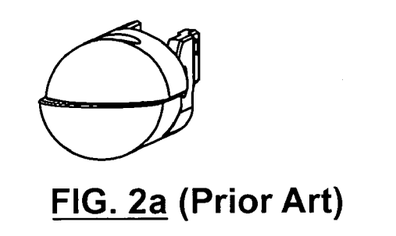
FIG. 2a illustrates in a perspective view lateral shift caused by poor repeatability of the thickness of the arm of the jaw and/or its location.
Figure 2B:
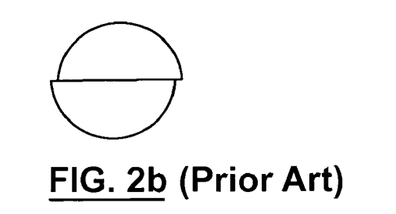
Figure 3:
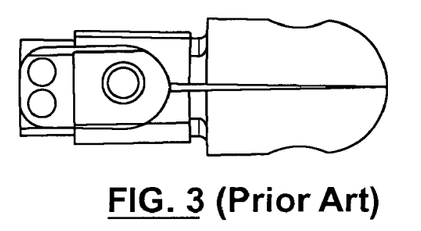
FIG. 3 illustrates in a side elevation view the problem of the tips of the cups meeting but the backs do not, creating a large gap on both sides of the jaws.
Figure 4:
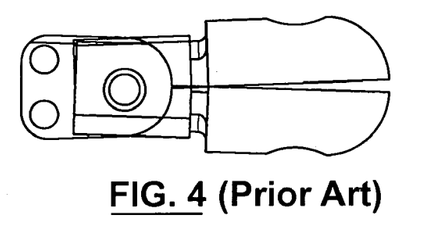
FIG. 4 illustrates in a side elevation view the problem of the tips of the cups do not meet, but the backs do, creating a large gap on both sides and the tip of the jaws.
Figure 5A:
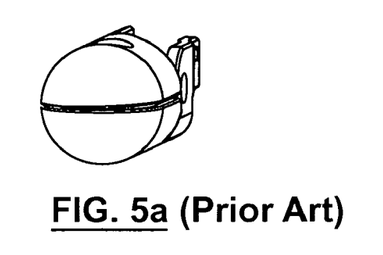
FIG. 5a illustrates in a perspective view the problem of the cutting edge of the jaws meeting on one side but not on the opposite side, thereby creating a gap.
Figure 5B:
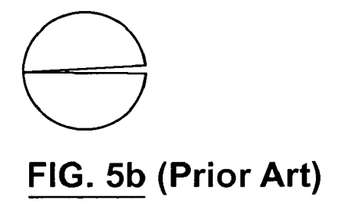
Figure 6:
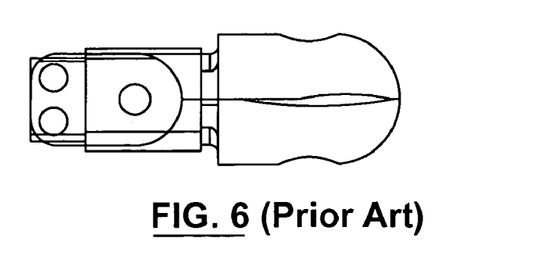
FIG. 6 illustrates in a side elevation view the problem of an irregular cutting plane and/or cutting edges, creating gaps between the jaws.
Figures 7, 8:
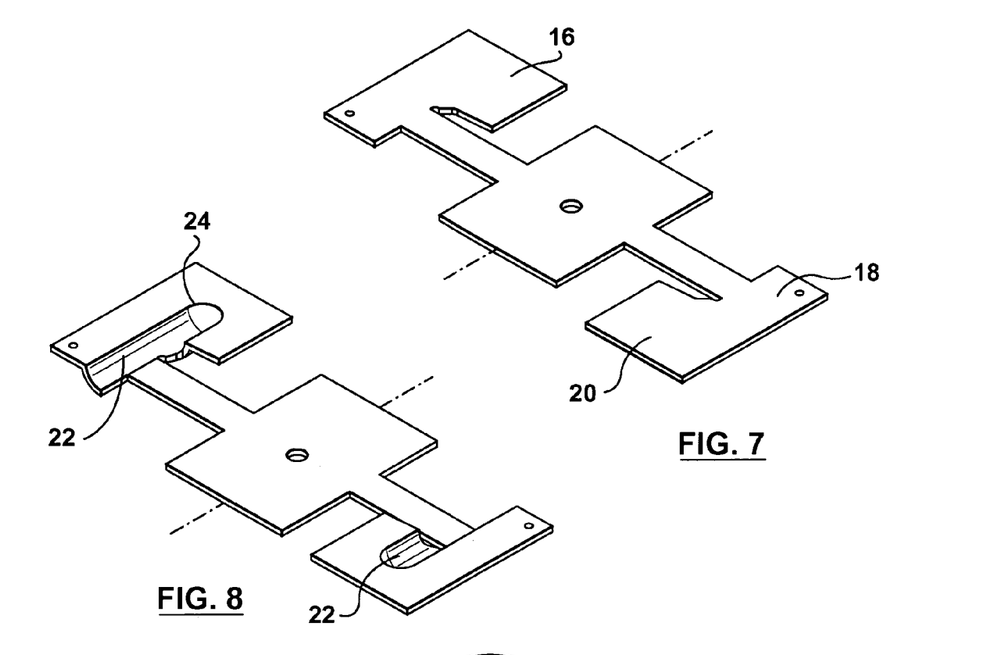
FIG. 7 illustrates in a perspective view, a strip of metal with two large shapes cut out for the method in accordance with a preferred embodiment of the present invention.
FIG. 8 in a perspective view, illustrates the drawing of the concave shaped cup portion for the method of the preferred embodiment of the present invention.
Figures 9, 10:
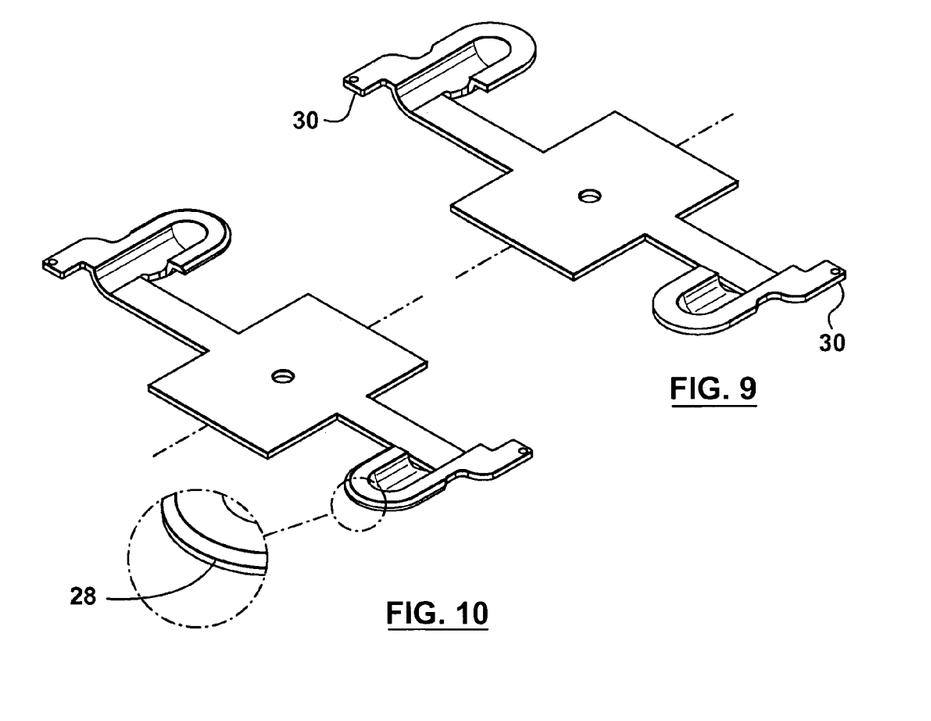
FIG. 9 is a perspective view of the cutting of the pattern of the preferred embodiment.
FIG. 10 is a perspective view of the preferred embodiment of FIG. 9 with a close up view of the cutting edge.

In accordance with the preferred embodiment of the preferred invention there is provided a method of progressive die stamping for manufacturing a biopsy forceps jaw. Referring to FIGS. 7–9, the method may comprise of the following steps of initially cutting a sheet 10 of metal into a strip 12. The strip of metal 12 may then be punched with a series of guide holes 14. The guide holes ensure accurate positioning of the strip of metal 12 in the progressive die (not shown) during the stamping and drawing process, or press working processes in general.

A shape 16 that is larger than the actual pattern of the biopsy forceps jaw is then cut or defined into the strip of metal 12. At this juncture in the method, the shape is still attached to the strip of metal. The shape 16 may have a proximal end 18 that is attached to the strip of metal 12 and a distal end 20.

The next step in the process involves drawing a concave shaped cup portion 22 of the biopsy forceps jaw. In general the formation of the concave shaped cup portion 22 is the step that represents the most severe deformation of the shape 16. As such it is important to ensure that the shape 16 and more particularly the immediate area 24 around the concave shaped cup portion 22 remains flat during this step. This positioning is ensured by the guide holes 14 and the application of the appropriate pressure by the blank holder (not shown) to area 24 during the stamping process. As such the drawing of the concave shaped cup portion 22 occurs with no wrinkling or rupture of the concave shaped cup portion 22.

The actual profile or pattern 26 of the biopsy forceps jaw 32 may then be cut thereby defining the concave shaped cup portion 22 and exposing a cutting edge 28 and exposed edges 30 of the pattern 26. By cutting the pattern 26 at this point during the process, an accurate or precise biopsy forceps jaw 32 results since the most severe deformation of the pattern 26 has already occurred. By producing the biopsy forceps jaw 32 in this way, the current invention overcomes the issue of overbite where one jaw is longer than the other as well as the problem of irregular cutting planes or cutting edges that cause gaps between the jaws.

Figures 11, 12:
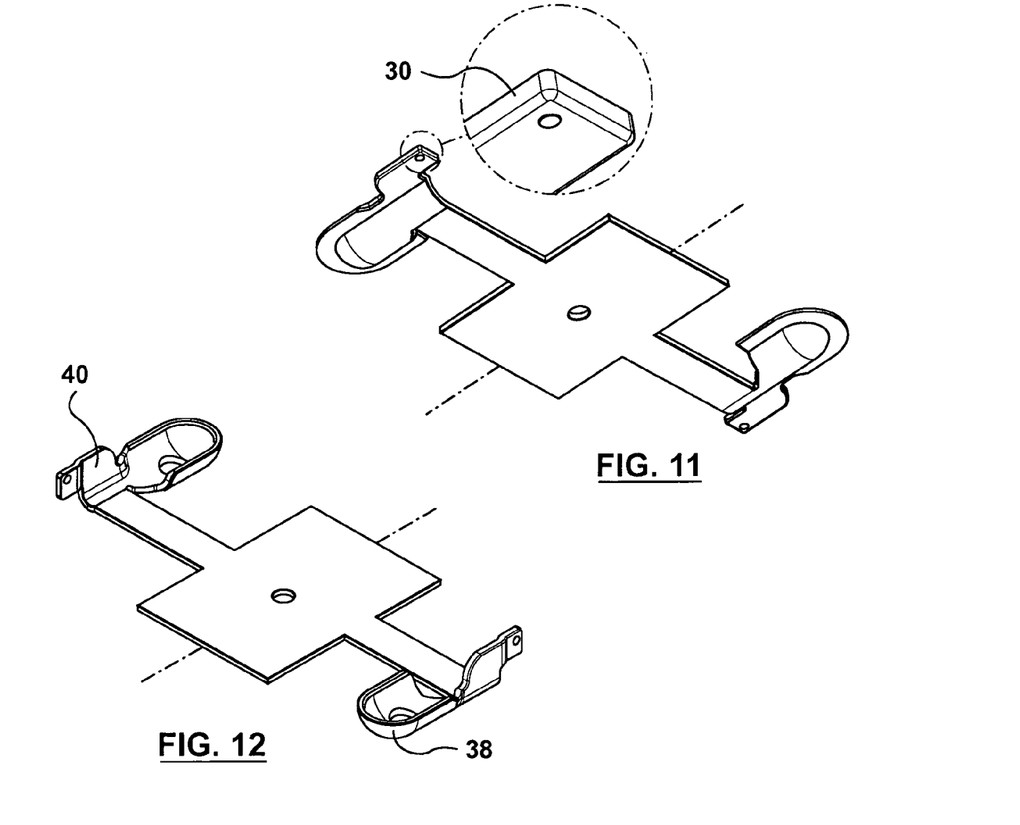
FIG. 11 is a bottom plan view of the preferred embodiment of FIG. 10 with a close up view of the chamfered exposed edges.
FIG. 12 is a perspective view of the folding and shaping step in accordance with the preferred embodiment of the present invention.
Figures 15A, 15B, 15C:
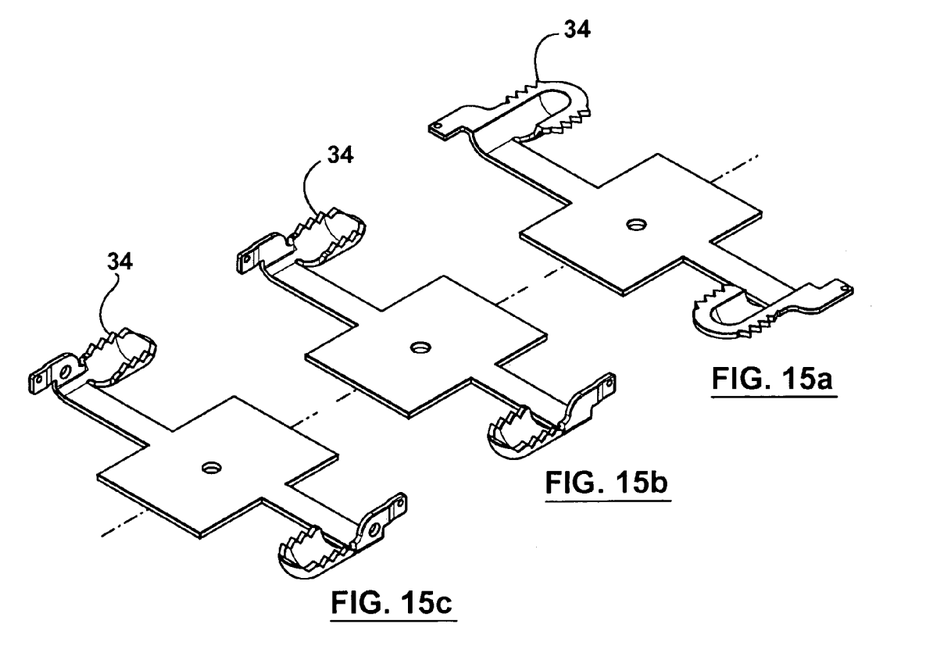
FIGS. 15a, 15b and 15c are perspective views in accordance with a second preferred embodiment of the present invention illustrating the method with unsharpened teeth.
Figures 16, 17:
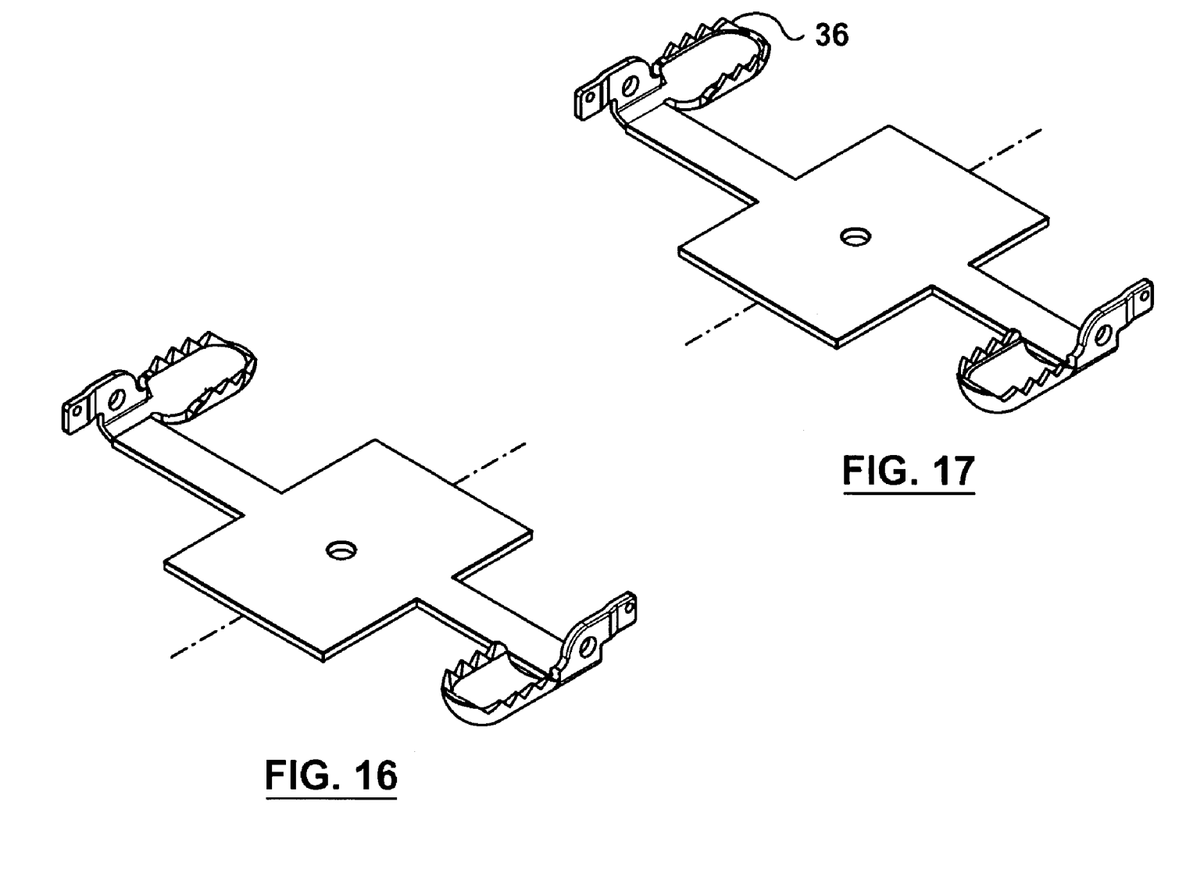
FIG. 16 is a perspective view illustrating sharpened teeth in accordance with a third preferred embodiment of the present invention.
FIG. 17 is a perspective view illustrates "thinned" teeth in accordance with a fourth preferred embodiment of the present invention.

Referring to FIGS. 10–12 in an alternative embodiment the method described above may further comprise the following step of coining the cutting edge 28 to provide a hardened, sharp, cutting edge. This step may be omitted and the cutting edge 28 may be serrated instead to form teeth 34 that are not sharpened as illustrated in FIGS. 15a–c. Furthermore, the cutting edge 28 may also be coined to thin the cutting edge 36, and then serrated or a combination thereof depending on the desired biting profile of the biopsy forceps jaw 32 as illustrated in FIGS. 16 and 17. In other words the biopsy forceps jaw 32 may also have sharpened serrated teeth 34. The exposed edges 30 resulting from the cutting of the pattern 26 may now be chamfered to debur or remove and rough edges that could potentially damage the passage of the biopsy forceps device.

Figure 13:
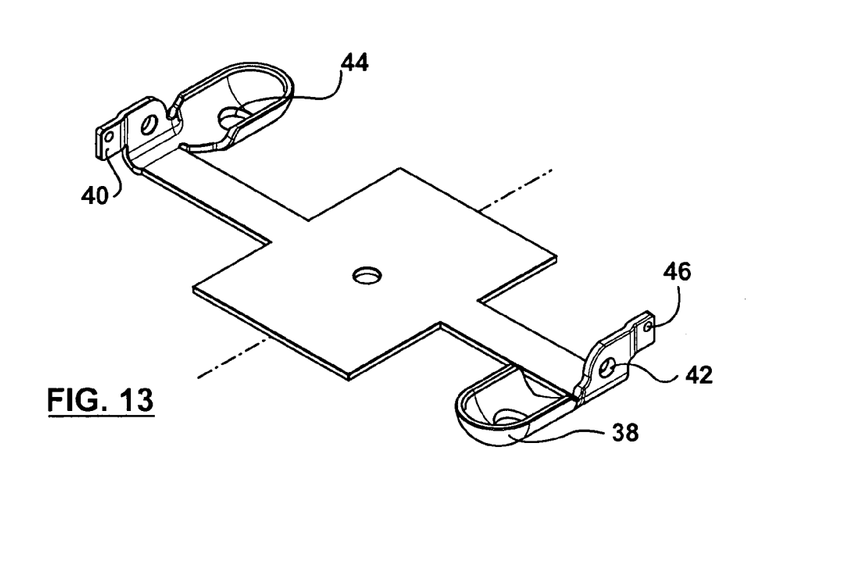
FIG. 13 is a perspective view of the pivot hole step in accordance with the preferred embodiment of the present invention.

Referring to FIGS. 12 and 13, in the next step, the pattern 26 may then be folded and shaped to form a biopsy forceps jaw cup. The pattern 26 may then be folded to position at least one arm 40 relative to the biopsy forceps jaw cup 38. The steps of folding and shaping the biopsy forceps jaw cup 38 and the arm 40 may be done independently or simultaneously. In general the arm 40 of the biopsy forceps jaw cup 38 is positioned upwards or perpendicular to biopsy forceps jaw cup 38 itself. By following the step outlined above, the instant invention overcomes lateral shift caused by poor repeatability of the thickness of the arm of the biopsy forceps jaw and/or its location. Furthermore, the instant invention overcomes having the cutting edge of the biopsy forceps jaws meet on one side but not on the opposite side thereby creating a gap resulting from poor control of the perpendicularity of the cutting plane of the biopsy forceps jaws relative to the plane of the arm or the twisting of the biopsy forceps jaw cup versus the arm of the biopsy forceps jaw.

At least one pivot hole 42 or holes may then be punched into the arm 40 of the biopsy forceps jaw 32. Once again the positioning of the strip of metal 12 by the guide holes 14 and the ability to control and adjust the instant stamping process, avoids the pivot hole 42 being located above or below the plane of the cutting edge, and therefore avoids problems with the tips or the backs of the biopsy forceps jaw cups not meeting and thereby creating a gap on both sides of the jaws.

Figure 14:
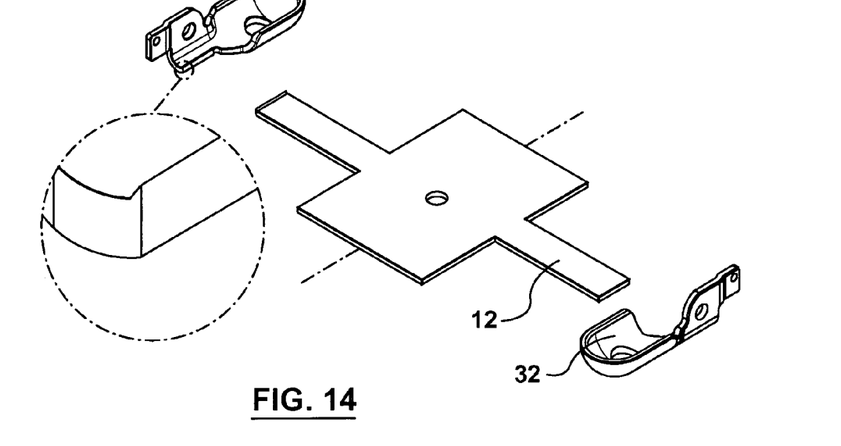
FIG. 14 is a perspective view of the biopsy forceps jaw being cut from the strip and a close up view of the cut off location and any possible bur protruding inwards on the device in accordance with the preferred embodiment of the present invention.

In the next step, the biopsy forceps jaw 32 may then go through a calibration by the die/punch arrangement so that the cutting edge 28 is on a plane perpendicular to a plane of the arm 40 of the biopsy forceps jaw 32. In the final step of the process, the biopsy forceps jaw 32 may be cut off of the strip of metal 12 in such a manner that any burr resulting from the cut off would protrude inwards on the biopsy forceps jaw 12.

The method may also include punching at least one fenestration hole 44 in the bottom of the concave shaped cup portion 22 of the biopsy forceps jaw 32. At least one actuating hole 46 may then be punched into the distal end 20 of the shape 16. The actuating hole 46 or holes may be small in nature and will eventually represent the hole that is located on the arm 40 of the biopsy forceps jaw 32 and accepts actuating wires for a biopsy forceps device. Furthermore, the pattern 26 may be cut to include a second arm or lobe, or multiple arms on the biopsy forceps jaw depending on the desired configuration.

Figures 18A, 18B, 18C, 18D, 18E, 18F, 18G, 18H, 18I:
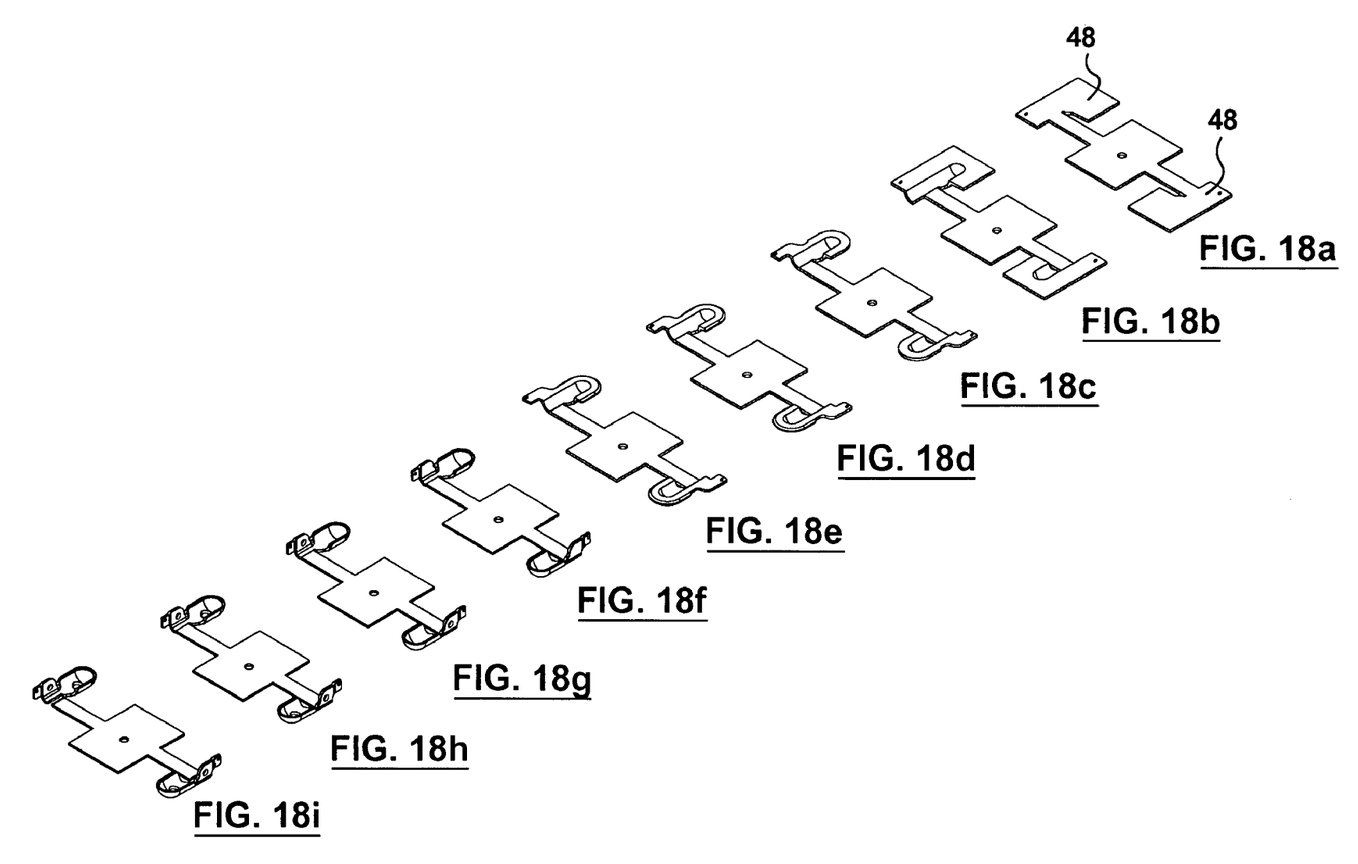

Finally referring to FIGS. 18a–c the strip of metal 12 may have two shapes 48 running parallel to one another. This ability is important as there are some important factors in progressive stamping which are beyond the control of the tooling and the manufacturing sequence. These are the variances in physical properties of the metal strip, such as ductility, as well as, the variance in the thickness of the metal strip.

These variances usually demonstrate themselves in a gradual manner along the length of the strip. Usually the individual jaws in the biopsy forceps jaws assembly are not exactly the same. As an example one jaw can be sharper than the other in order to facilitate the "knife and board" cutting principle, or in case of the serrated jaws, the teeth may be shifted so they can intermesh, when the jaws are closed.

In order to minimize the input of the strip variances, the jaws (upper/lower, left/right) are produced by the described method in a parallel configuration on the same strip. Close proximity of the jaws assures that they are produced from a strip of identical physical and geometrical properties.

The finished biopsy forceps jaws can be picked-up after cut-off in pairs, or more practically in lots of limited numbers, say one thousand pairs as an example. The size of the lot can be determined through empirical methods. This way we will minimize or eliminate the input of the variances of the strip and maintain desired precision of the parts.

Other variations and modifications of the invention are possible. All such modifications or variations are believed to be within the sphere and scope of the invention as defined by the claims appended hereto.

I claim:

1. A method of progressive die stamping manufacturing a biopsy forceps jaw comprising:
   (a) Cutting a sheet of metal into a strip;
   (b) Punching a series of guide holes into said strip of metal;
   (c) Defining in said strip of metal a shape larger than a pattern of said biopsy forceps jaw, said shape having a proximal end and a distal end whereby said shape is attached to said strip of metal;
   (d) Drawing said distal end of said shape into at least a part of a concave shaped cup portion of said biopsy jaws;
   (e) Cutting said pattern of said biopsy forceps jaw around said concave shaped cup portion to expose a cutting edge and exposed edges;
   (f) Folding and shaping said pattern to form a biopsy forceps jaw cup and at least one arm positioned relative to said biopsy forceps jaw cup;
   (g) Punching at least one pivot hole into said arm;
   (h) Coining said cutting edge to provide a hardened, sharp, cutting edge prior to folding and shaping said pattern;
   (i) Coining said pattern to chamfer said exposed edges prior to folding and shaping said pattern;
   (j) Punching at least one actuating hole at said distal end of said shape prior to drawing said concave shaped cup portion;

(k) Calibrating said biopsy forceps jaw whereby said cutting edge is on a plane perpendicular to a plane of said arm; and (l) Cutting said biopsy forceps jaw cup off of said strip of metal in such a manner that any burr created during the cut off protrudes inward.

2. A method of progressive die stamping manufacturing a biopsy forceps jaw as claimed in claim 1 further comprising serrating said hardened, sharp, cutting edge to form teeth.

3. A method of progressive die, stamping manufacturing a biopsy forceps jaw as claimed in claim 1 further comprising punching at least one fenestration hole in said concave shaped cup portion of said biopsy forceps jaw.

4. A method of progressive die stamping manufacturing a biopsy forceps jaw as claimed in claim 1 further comprising folding said pattern to form said biopsy forceps jaw cup in a separate step from positioning said arm relative to biopsy forceps jaw cup.

5. A method of progressive die stamping manufacturing a biopsy forceps jaw as claimed in claim 1 wherein said pattern of said biopsy forceps jaw defines at least two arms.

6. A method of progressive die stamping manufacturing a biopsy forceps jaw as claimed in claim 1 wherein said strip of metal has at least two patterns of said biopsy forceps jaws running parallel to one another and connected to said strip of metal.

7. A method of progressive die stamping manufacturing a biopsy forceps jaw comprising:

(a) Cutting a sheet of metal into a strip of metal;

(b) Punching a series of guide holes into said strip of metal;

(c) Defining in said scrip of metal a shape larger than a pattern of said biopsy forceps jaw, said shape having a proximal end and a distal end whereby said shape is attached to said strip of metal;

(d) Punching at least one actuating hole at said distal end of said shape;

(e) Drawing said distal end of said shape into at least a pan of a concave shaped cup portion of said biopsy forceps jaw;

(f) Cutting said pattern of said biopsy forceps jaw around said concave shaped cup portion to expose a cutting edge and exposed edges;

(g) Coining said cutting edge thereby thinning said cutting edge;

(h) Coining said pattern to chamfer said exposed edges;

(i) Folding and shaping said pattern to form a biopsy forceps jaw cup and at least one arm positioned relative to said biopsy forceps jaw cup;

(j) Punching at least one pivot hole into said arm;

(k) Calibrating said biopsy forceps jaw whereby said cutting edge is on a plane perpendicular to a plane of said arm; and (l) Cutting said biopsy forceps jaw cup off of said strip of metal in such a manner that any burr created during the cut-off protrudes inward.

8. A method of progressive die stamping manufacturing a biopsy forceps jaw as claimed in claim 7 further comprising serrating said thinned cutting edge to form teeth.

9. A method of progressive die stamping manufacturing a biopsy forceps jaw as claimed in claim 7 further comprising punching at least one fenestration hole in said concave shaped cup portion of said biopsy forceps jaw.

10. A method of progressive die stamping manufacturing a biopsy forceps jaw as claimed in claim 7 further comprising folding said pattern to form said biopsy forceps jaw cup in a separate step from positioning said arm relative to biopsy forceps jaw cup.

11. A method of progressive die stamping manufacturing a biopsy forceps jaw as claimed in claim 7 wherein said pattern of said biopsy forceps jaw defines at least two arms.

12. A method of progressive die stamping manufacturing a biopsy forceps jaw as claimed in claim 7 wherein said strip of metal has at least two patterns of said biopsy forceps jaws running parallel to one another and connected to said strip of metal.

13. A method of progressive die stamping manufacturing a biopsy forceps jaw comprising:

(a) Cutting a sheet of metal into a strip;

(b) Punching a series of guide holes into said strip of metal;

(c) Defining in said strip of metal a shape larger than a pattern of said biopsy forceps jaw, said shape having a proximal end and a distal end whereby said shape is attached to said metal strip;

(d) Punching at least one actuating hole at said distal end of said shape;

(e) Drawing said distal end of said shape into at least a part of a concave shaped cup portion of said biopsy forceps jaw;

(f) Cutting said pattern of said biopsy forceps jaw around said concave shaped cup portion to expose a cutting edge wherein said cutting edge is serrated and exposed edges;

(g) Coining said pattern to chamfer said exposed edges;

(h) Folding and shaping said pattern to form a biopsy forceps jaw cup and at least one arm positioned relative to said biopsy forceps jaw cup;

(i) Punching at least one pivot hole into said arm;

(j) Calibrating said biopsy forceps jaw whereby said cutting edge is on a plane perpendicular to a plane of said arm; and (k) Cutting said biopsy forceps jaw cup off of said metal strip in such a manner that any burr created during the cut-off protrudes inward.

14. A method of progressive die stamping manufacturing a biopsy forceps jaw as claimed in claim 13 further comprising punching at least one fenestration, hale in said concave shaped cup portion of said biopsy forceps jaw.

15. A method of progressive die stamping manufacturing a biopsy forceps jaw as claimed in claim 13 further comprising folding said pattern to form said biopsy forceps jaw cup in a separate step from positioning said arm relative to biopsy forceps jaw cup.

16. A method of progressive die stamping manufacturing a biopsy forceps jaw as claimed in claims 13 wherein said pattern of said biopsy forceps jaw defines at least two arms.

17. A method of progressive die stamping manufacturing a biopsy forceps jaw as claimed in claim 13 wherein said strip of metal has at least two patterns of said biopsy forceps jaws running parallel to one another and connected to said strip of metal.

18. A method of progressive die stamping manufacturing a biopsy forceps jaw comprising:

(a) Cutting a sheet of metal into a strip;

(b) Punching a series of guide holes into said strip of metal;

(c) Defining in said strip of metal a shape larger than a pattern of said biopsy forceps jaw, said shape having a proximal end and a distal end whereby said shape is attached to said metal strip;

(d) Punching at least one actuating hole at said distal end of said shape;

(e) Drawing said distal end of said shape into at least a part of a concave shaped cup portion of said biopsy forceps jaw;

(f) Cutting said pattern of said biopsy forceps jaw around said concave shaped cup portion to expose a cutting edge of a desired profile and exposed edges;

(g) Coining said pattern to chamfer said exposed edges;

(h) Folding and shaping said pattern to form a biopsy forceps jaw cup and at least one arm positioned relative to said biopsy forceps jaw cup;

(I) Punching at least one pivot hole into said arm;

(j) Calibrating said biopsy forceps jaw whereby said cutting edge is on a plane perpendicular to a plane of said arm; and (k) Cutting said biopsy forceps jaw cup off of said strip in such a manner that any burr created during the cut-off protrudes inward.

19. A method of progressive die stamping manufacturing a biopsy forceps jaw as claimed in claim 18, further comprising coining said cutting edge of said desired profile to a hardened, sharp, cutting edge.

20. A method of progressive die stamping manufacturing a biopsy forceps jaw as claimed in claim 18 further comprising punching at least one fenestration hole in said concave shaped cup portion of said biopsy forceps jaw.

21. A method of progressive die stamping manufacturing a biopsy forceps jaw as claimed in claim 18 further comprising folding said pattern to form said biopsy forceps jaw cup in a separate step from positioning said arm relative to said biopsy forceps jaw cup.

22. A method of progressive die stamping manufacturing a biopsy forceps jaw as claimed in claim 18 wherein said pattern of said biopsy forceps jaw defines at least two arms.

23. A method of progressive die stamping manufacturing a biopsy forceps jaw as claimed in claim 18 wherein said strip of metal has at least two patterns of said biopsy forceps jaws running parallel to one another and connected to said strip of metal.

24. A method of progressive die stamping manufacturing of a cup portion of a biopsy forceps jaw comprising:

(a) Defining a sheet of metal into a strip;

(b) Defining a series of guides into said strip of metal;

(c) Defining in said strip of metal a shape [larger than a pattern of said biopsy forceps jaw, said shape having a proximal end and a distal end] having a proximal end and a distal end, at least the distal end of the shape being larger then a pattern of the cup portion of the biopsy forceps jaw and at least the distal end of the shape being continuously defined;

(d) At least partially drawing, said distal end of said shape into at least a pan of a concave shaped cup portion of said biopsy forceps jaws;

(e) Defining at least partially said pattern of said biopsy forceps jaw to expose at least an edge of a desired cup profile around said concave shaped cup portion; and (f) Folding and shaping said pattern to form at least the cup portion of a biopsy, forceps jaw.

25. A method progressive die stamping manufacturing of a cup portion of a biopsy forceps jaw as claimed in claim 24 wherein the edge is serrated.

26. A method of progressive die stamping manufacturing a biopsy forceps jaw as claimed in claim 2 further comprising punching at least one fenestration hole in said concave shaped cup portion of said biopsy forceps jaw.

27. A method of progressive die stamping manufacturing a biopsy forceps jaw as claimed in claim 2 further comprising folding said pattern to form said biopsy forceps jaw cup in a separate step from positioning said arm relative to biopsy forceps jaw cup.

28. A method of progressive die stamping manufacturing a biopsy forceps jaw as claimed in claim 2 wherein said pattern of said biopsy forceps jaw defines at least two arms.

29. A method of progressive die stamping manufacturing a biopsy forceps jaw as claimed in claim 2 wherein said strip of metal has at least two patterns of said biopsy forceps laws running parallel to one another and connected to said strip of metal.

30. A method of progressive die stamping manufacturing a biopsy forceps jaw as claimed in claim 3 further comprising folding said pattern to form said biopsy forceps jaw cup in a separate step from positioning said arm relative to biopsy forceps jaw cup.

31. A method of progressive die stamping manufacturing a biopsy forceps jaw as claimed in claim 3 wherein said pattern of said biopsy forceps jaw defines at least two arms.

32. A method of progressive die stamping manufacturing a biopsy forceps jaw as claimed in claim 3 wherein said strip of metal has at least two patterns of said biopsy forceps laws running parallel to one another and connected to said strip of metal.

33. A method of progressive die stamping manufacturing a biopsy forceps jaw as claimed in claim 4 wherein said pattern of said biopsy forceps jaw defines at least two arms.

34. A method of progressive die stamping manufacturing a biopsy forceps jaw as claimed in claim 4 wherein said strip of metal has at least two patterns of said biopsy forceps jaws running parallel to one another and connected to said strip of metal.

35. New A method of progressive die stamping manufacturing a biopsy forceps jaw as claimed in claim 5 wherein said strip of metal has at least two patterns of said biopsy forceps jaws running parallel to one another and connected to said strip of metal.

36. A method of progressive die stamping manufacturing a biopsy forceps jaw as claimed in claim 8 further comprising punching at least one fenestration hole in said concave shaped cup portion of said biopsy forceps jaw.

37. A method of progressive die stamping manufacturing a biopsy forceps jaw as claimed in claim 8 further comprising folding said pattern to form said biopsy forceps jaw cup in a separate step from positioning said arm relative to biopsy forceps jaw cup.

38. A method of progressive die stamping manufacturing biopsy forceps jaw as claimed in claim 8 wherein said pattern of said biopsy forceps jaw defines at least two arms.

39. A method of progressive die stamping manufacturing a biopsy forceps jaw as claimed in claim 8 wherein said strip of metal has at least two patterns of said biopsy forceps jaws running parallel to one another and connected to said strip of metal.

40. A method of progressive die stamping manufacturing a biopsy forceps jaw as claimed in claim 9 further comprising folding said pattern to form said biopsy forceps jaw cup in a separate step from positioning said arm relative to biopsy forceps jaw cup.

41. A method of progressive die stamping manufacturing a biopsy forceps jaw as claimed in claim 9 wherein said pattern of said biopsy forceps jaw defines at least two arms.

42. A method of progressive die stamping manufacturing a biopsy forceps jaw as claimed in claim 9 wherein said strip of metal has at least two patterns of said biopsy forceps jaws running parallel to one another and connected to said strip of metal.

43. A method progressive die stamping manufacturing a biopsy forceps jaw as claimed in claim 10 wherein said pattern of said biopsy forceps jaw defines at least two arms.

44. A method of progressive die stamping manufacturing a biopsy forceps jaw as claimed in claim 10 wherein said strip of metal has at least two patterns of said biopsy forceps jaws running parallel to one another and connected to said strip of metal.

45. A method of progressive die stamping manufacturing biopsy forceps jaw as claimed in claim 11 wherein said strip of metal has at least two patterns of said biopsy forceps jaws running parallel to one another and connected to said strip of metal.

46. A method of progressive die stamping manufacturing a biopsy forceps jaw as claimed in claim 14 further comprising folding said pattern to form said biopsy forceps jaw cup in a separate step from positioning said arm relative to biopsy forceps jaw cup.

47. A method of progressive die stamping manufacturing a biopsy forceps jaw as claimed in claim 14 wherein said pattern of said biopsy forceps jaw defines at least two arms.

48. A method of progressive die stamping manufacturing a biopsy forceps jaw as claimed in claim 14 wherein said strip of metal has at least two patterns of said biopsy forceps jaws running parallel to one another and connected to said strip of metal.

49. A method of progressive die stamping manufacturing a biopsy forceps jaw as claimed in claim 15 wherein said strip of metal has at least two patterns of said biopsy forceps jaws running parallel to one another and connected to said strip of metal.

50. A method of progressive die stamping manufracturing a biopsy forceps jaw as claimed in claim 15 wherein said strip of metal has at least two patterns of said biopsy forceps jaws running parallel to one another and connected to said strip of metal.

51. A method of progressive die stamping manufacturing a biopsy forceps jaw as claimed in claim 16 wherein said strip of metal has at least two patterns of said biopsy forceps jaws running parallel to one another and connected to said strip of metal.

52. A method of progressive die stamping manufacturing a biopsy forceps jaw as claimed in claim 20 further comprising punching at least one fenestration hole in said concave shaped cup portion of said biopsy forceps jaw.

53. A method of progressive die stamping manufacturing a biopsy forceps jaw as claimed in claim 20 further comprising folding said pattern to form said biopsy forceps jaw cup in a separate step from positioning said arm relative to biopsy forceps jaw cup.

54. A method of progressive die stamping manufacturing a biopsy forceps jaw as claimed in claim 20 wherein said pattern of said biopsy forceps jaw defines at least two arms.

55. A method of progressive die stamping manufacturing biopsy forceps jaw as claimed in claim 20 wherein said strip of metal has at least two patterns of said biopsy forceps jaws running parallel to one another and connected to said strip of metal.

56. A method of progressive die stamping manufacturing a biopsy forceps jaw as claimed in claim 21 further comprising folding said pattern to form said biopsy forceps jaw cup in a separate step from positioning said arm relative to biopsy forceps jaw cup.

57. A method of progressive die stamping manufacturing a biopsy forceps jaw as claimed in claim 21 wherein said pattern of said biopsy forceps jaw defines at least two arms.

58. A method of progressive die stamping manufacturing a biopsy forceps jaw as claimed in claim 21 wherein said strip of metal has at least two patterns of said biopsy forceps jaws running parallel to one another and connected to said strip of metal.

59. A method of progressive die stamping manufacturing a biopsy forceps jaw as claimed in claim 22 wherein said pattern of said biopsy forceps jaw defines at least two arms.

60. A method of progressive die stamping manufacturing a biopsy forceps jaw as claimed in claim 22 wherein said strip of metal has at least two patterns of said biopsy forceps jaws running parallel to one another and connected to said strip of metal.

61. A method of progressive die stamping manufacturing a biopsy forceps jaw as claimed in claim 26 wherein said strip of metal has at least two patterns of said biopsy forceps jaws running parallel to one another and connected to said strip of metal.

62. A method of progressive die stamping manufacturing of a cup portion of a biopsy forceps jaw as claimed in claim 24 wherein the cutting edge is coined to provide hardened, sharp cutting edge.

63. A method of progressive die stamping manufacturing of a cup portion of a biopsy forceps jaw as claimed in claim 24 wherein the cutting edge is serrated and coined to provide hardened, sharp, serrated cutting edge.

64. A method of progressive die stamping manufacturing of a cup portion of a biopsy forceps jaw as claimed in claim 24 further compromising punching at least one fenestration hole in said concave shaped cup portion of said biopsy forceps jaw.

* * * * *